United States Patent
Van Der Ploeg et al.

(10) Patent No.: US 11,049,492 B2
(45) Date of Patent: Jun. 29, 2021

(54) SYSTEMS AND METHODS FOR TRANSPOSING SPOKEN OR TEXTUAL INPUT TO MUSIC

(71) Applicant: YAO THE BARD, LLC, Plymouth, MA (US)

(72) Inventors: Leonardus H. T. Van Der Ploeg, Newton, MA (US); Halley Young, Philadelphia, PA (US)

(73) Assignee: YAO THE BARD, LLC, Plymouth, MA (US)

( * ) Notice: Subject to any disclaimer, the term of this patent is extended or adjusted under 35 U.S.C. 154(b) by 0 days.

(21) Appl. No.: 17/094,164

(22) Filed: Nov. 10, 2020

(65) Prior Publication Data
US 2021/0056952 A1 Feb. 25, 2021

Related U.S. Application Data

(60) Provisional application No. 62/815,001, filed on Mar. 7, 2019.

(51) Int. Cl.
*G10L 13/08* (2013.01)

(52) U.S. Cl.
CPC .................. *G10L 13/08* (2013.01)

(58) Field of Classification Search
None
See application file for complete search history.

(56) References Cited

U.S. PATENT DOCUMENTS

| | | | |
|---|---|---|---|
| 5,796,916 A * | 8/1998 | Meredith | G10L 13/10 704/207 |
| 9,564,123 B1 * | 2/2017 | Mont-Reynaud | H04L 67/306 |
| 2003/0023421 A1 | 1/2003 | Finn et al. | |
| 2004/0023191 A1 * | 2/2004 | Brown | G09B 17/00 434/156 |
| 2005/0182616 A1 | 8/2005 | Kotipalli | |
| 2008/0319755 A1 | 12/2008 | Nishiike et al. | |
| 2013/0000465 A1 | 1/2013 | Gurule | |
| 2014/0039871 A1 * | 2/2014 | Crawford | G06F 40/103 704/2 |
| 2018/0012508 A1 * | 1/2018 | Sulkin | G09B 19/003 |

FOREIGN PATENT DOCUMENTS

WO 2020/181234 A1 9/2020

OTHER PUBLICATIONS

Vicente et al. "From heuristics-based to data-driven audio melody extraction." In: Diss. Universitat Pompeu Fabra, Jun. 27, 2017.
Deutsch et al. "The speech-to-song illusion." In: The Journal of the Acoustical Society of America. Nov. 11, 2008.
Rizo et al. "Melody Track Identification in Music Symbolic Files." In: FLAIRS Conference. Jan. 2006.
International Search Report and Written Opinion for Application No. PCT/US2020/021495 dated Jul. 22, 2020.

* cited by examiner

*Primary Examiner* — Jakieda R Jackson
(74) *Attorney, Agent, or Firm* — Lando & Anastasi, LLP

(57) ABSTRACT

Described herein are real-time musical translation devices (RETM) and methods of use thereof. Exemplary uses of RETMs include optimizing the understanding and/or recall of an input message for a user and improving a cognitive process in a user.

33 Claims, 8 Drawing Sheets

SYSTEMS AND METHODS FOR TRANSPOSING SPOKEN OR TEXTUAL INPUT TO MUSIC

CROSS-REFERENCE TO RELATED APPLICATION

This application is a continuation of International Application No. PCT/US2020/021495 titled "SYSTEMS AND METHODS FOR TRANSPOSING SPOKEN OR TEXTUAL INPUT TO MUSIC," filed Mar. 6, 2020, which claims priority under 35 U.S.C. § 119(e) to U.S. Provisional Application Ser. No. 62/815,001 titled "SYSTEMS AND METHODS FOR TRANSPOSING SPOKEN OR TEXTUAL INPUT TO MUSIC," filed Mar. 7, 2019, which is incorporated herein by reference in its entirety for all purposes.

TECHNICAL FIELD

The present disclosure is directed to systems and methods for transposing spoken or textual input to music.

BACKGROUND

For millennia, humans have used music, and in particular vocal songs and melodies, to convey information in a manner that heightens interest and facilitates comprehension and long-term recall of the information conveyed. The timing and variations in pitch and rhythm in a song may signal to the listener what information is important and how different concepts in the text are related to each other, causing the listener to retain and understand more of the information than if it was merely spoken. The unique ability of song to convey information that is distinctly processed by the brain from non-musical spoken words is supported by brain imaging results which have shown that different patterns of brain activity occur for spoken words when compared to words in song. The findings highlighting unique cognitive processing of words in song, are supported by applications where, in addition to their entertainment value, songs may be taught to children to assist with learning and remembering the number of days in a month, the states and their capitals, or other pieces of information that may otherwise elude understanding or memory retention.

Separately, but relatedly, persons with a cognitive impairment, behavioral impairment, or learning impairment may find it easier to comprehend and recall information when conveyed as a song or melody. For example, a passage of text read in a normal speaking tone by the student or an instructor may not be comprehended or recalled, whereas the same passage of text when sung may be more easily comprehended and recalled by persons having impairments including, for example, dyslexia, aphasia, autism spectrum disorder, Alzheimer's disease, dementia, Down's syndrome, Prader Willi syndrome, Smith Magenis syndrome, indications that include learning disability and/or intellectual disability, Parkinson's disease, anxiety, stress, schizophrenia, brain surgery, surgery, stroke, trauma, or other neurological disorder. Exposure to information "coded" in music is anticipated to lead, over the long term, to enhanced verbal IQ, quantitative measures of language comprehension, and quantitative measures of the ability to interact with care providers.

While users with selected clinical impairments may benefit from information being sung, the general population of instructors, care providers, teachers and the like may not have the capability or willingness to sing the information to be conveyed. Even if instructors do have such willingness and skills, transforming text or voice to a musical score takes time and effort if word recognition and comprehension are to be optimally retained. Furthermore, for the case of text, the instructor's physical presence could be required for the text to be heard. In addition, different individuals and/or different disorders may respond to different styles and natures of music (i.e., genre, tempo, rhythm, intervals, key, chord structure, song structure), meaning that even for a given passage of information, a one-size-fits-all approach may be inadequate. While it is possible to compose, pre-record and play back information being sung, such an arrangement is inflexible in that it does not allow for the music or the information being conveyed to be adjusted in real time, or near real time, such as in response to student questions or needs.

SUMMARY

A device and/or software are provided for receiving real-time or near-real-time input (e.g., a textual, audio, or spoken message) containing information to be conveyed, and converting that input to a patterned musical message, such as a melody, intended to facilitate a learning or cognitive process of a user. The musical message may be performed in real-time or near-real time. In the examples described here, the application and device are described as a dedicated Real Time Musical Translation Device (RETM), wherein "device" should be understood to refer to a system that incorporates hardware and software components, such as mobile applications. It will be appreciated, however, that the application may also be performed on other audio-input and -output capable devices, including a mobile device such as a smart phone, tablet, laptop computer, and the like, that has been specially programmed.

The RETM may allow the user to have some control and/or selection regarding the musical themes that are preferred or that can be chosen. For example, a user may be presented with a list of musical genres, moods, styles, or tempos, and allowed to filter the list of songs according to the user's selection, which will be taken to transfer routine spoken words or text to the musical theme, in real or near-real time. In another example, the user may identify one or more disorders that the patterned musical message is intended to be adapted for, and the RETM may select a genre and/or song optimized for that disorder. In yet another example, a user may be "prescribed," by a medical care provider, a genre suitable for treating the user's disorder. It will be appreciated that as used herein, "genre" is intended to encompass different musical styles and traditions originating from different time periods, locations, or cultural groups, as well as systematic differences between artists within a given time period. Genres may include, for example, rock, pop, R&B, hip-hop, rap, country, nursery rhymes, or traditional music such as Gregorian chants or Jewish Psalm tones, as well as melodies fitting a particular class of tempo ("slow", "medium", or "fast"), mood ("cheerful", "sad", etc.), or predominant scale ("major" or "minor") or other quantifiable musical property. User preferences, requirements, and diagnoses may be learned and stored by the device, such that an appropriate song or genre may be suggested and/or selected by the RETM in an intuitive and helpful manner. In some embodiments, machine learning and/or artificial intelligence algorithms may be applied to enable the RETM to learn, predict, and/or adapt to user preferences, requirements, and diagnoses including collecting and applying user-data that describe a user's physiological condition including heart rate, eye movements, breathing, muscle-tone, movement, pharmacodynamic markers of RETM efficacy.

In some embodiments, the selections regarding genre and/or disorder may be used to match portions of a timed text input to appropriate melody segments in order to generate a patterned musical message.

It will be appreciated that while the patterned musical message generated and output by the RETM is referred to here as a "melody" for the sake of simplicity, the patterned musical message is not necessarily a melody as defined in musical theory, but may be any component of a piece of music that when presented in a given musical context is musically satisfying and/or that facilitates word or syntax comprehension or memory, including rhythm, harmony, counterpoint, descant, chant, particular spoken cadence (e.g., beat poetry), or the like, as exemplified in rhythmic training, phonemic sound training or general music training for children with dyslexia. It will also be appreciated that the musical pattern may comprise an entire song, one or more passages of the song, or simply a few measures of music, such as the refrain or "hook" of a song. More generally, music may be thought of in this context as the melodic transformation of real-time spoken language or text to known and new musical themes by ordering tones and sounds in succession, in combination, and in temporal relationships to produce a composition having unity and continuity. Relevant indications benefitting from the RETM include, for example, dyslexia, aphasia, autism spectrum disorder, Alzheimer's disease, dementia, Down's syndrome, Prader Willi syndrome, Smith Magenis syndrome, indications that include learning disability and/or intellectual disability, Parkinson's disease, anxiety, stress, schizophrenia, brain surgery, surgery, stroke, trauma, or other neurological disorder. For instance, in cases of stroke causing lesion to the left-hemisphere, particularly near language-related areas such as Broca's area, any patterning that leads to a more musical output, including all musical or prosodic components above, may lead to increased ability to rely on intact right-hemisphere function to attain comprehension. In the case of dyslexia, any one of these added musical dimensions to the text may provide alternative pathways for comprehension.

According to some embodiments, recognition and/or comprehension of the words presented in song can be over 95%, or over 99%, or over 99.5%, or over 99.9% using the methods and/or devices described herein. It will be appreciated that any significant improvement in comprehension can lead to significant improvements of quality of life in cases such as post-stroke aphasia, where patients will need to communicate with their caretakers and other individuals, in dyslexia, where individuals may be able to struggle less in educational settings, or for any of the above indications where quality of life is hindered by the inability to communicate or attain information through spoken or textual sources.

While scenarios involving an "instructor" and a "student" are described here for clarity purposes, it should be understood that the term "user" of the device, as referred to herein, encompasses any individual that may use the device, such as an instructor, a teacher, a physician, a nurse, a therapist, a student, a parent or guardian of said student, or a care provider. A user of the device may or may also be referred to herein as a "subject." A user may be a child or an adult, and may be either male or female. In an embodiment, the user is a child, e.g., an individual 18 years of age or younger.

In an embodiment, the user may have an indication described herein, such as a learning disability, Alzheimer's disease, or may be recovering from a stroke. Further, as the treatable conditions discussed herein are referred to generally as "disorders," it is to be appreciated that the RETM may be used to treat disabilities, afflictions, symptoms, or other conditions not technically categorized as disorders or the RETM may be used to facilitate general understanding and comprehension of routine conversation.

It is also to be appreciated that real-time translation of information to patterned musical messages may benefit typically developing/developed users as well as those with a disorder or other condition, e.g., as described. Furthermore, the real-time or near real-time translation of spoken or textual language to music made possible by these systems and methods provide advantages beyond the therapeutic uses discussed here. For example, the RETM may be used for musical or other entertainment purposes, including music instruction or games.

In one aspect, the present disclosure features a method of transforming textual input to a musical score comprising receiving text input; transliterating the text input into a standardized phonemic representation of the text input; and one or more of (i) determining for the phonemic text input, a plurality of spoken pause lengths and a plurality of spoken phoneme lengths; (ii) mapping the plurality of spoken pause lengths to a respective plurality of sung pause lengths; (iii) mapping the plurality of spoken phoneme lengths to a respective plurality of sung phoneme lengths; (iv) generating, from the plurality of sung pause lengths and the plurality of sung phoneme lengths, a timed text input; (v) generating a plurality of matching metrics for each of a respective plurality of portions of the timed text input against a plurality of melody segments, where programmed minor melody modifications (based on (i)-(v)) enhance song/text comprehension; and (vi) generating a patterned musical message from the timed text input and the plurality of melody segments based at least in part on the plurality of matching metrics. In an embodiment, the method comprises (i). In an embodiment, the method comprises (ii). In an embodiment, the method comprises (iii). In an embodiment, the method comprises (iv). In an embodiment, the method comprises (v). In an embodiment, the method comprises (vi). In an embodiment, the method comprises two of (i)-(vi). In an embodiment, the method comprises three of (i)-(vi). In an embodiment, the method comprises four of (i)-(vi). In an embodiment, the method comprises five of (i)-(vi). In an embodiment, the method comprises each of (i)-(vi).

The method may be performed in real-time or in near-real-time. In an embodiment, the method comprises causing the patterned musical message to be played audibly on a transducer. In an embodiment, the patterned musical message is expected to optimize, for a user, at least one of an understanding of the input message and a recall of the input message. In an embodiment, the method further comprises providing to a user a visual image relating to the patterned musical message aimed at enhancing comprehension and learning.

In some embodiment, the user has a cognitive impairment, a behavioral impairment, or a learning impairment. In an embodiment, the user has a comprehension disorder, including at least one of autism spectrum disorder, attention deficit disorder, attention deficit hyperactivity disorder, aphasia, dementia, dyspraxia, dyslexia, dysphasia, apraxia, stroke, traumatic brain injury, schizophrenia, schizoaffective disorder, depression, bipolar disorder, post-traumatic stress disorder, Alzheimer's disease, Parkinson's disease, age-related cognitive impairment, brain surgery, surgery, a language comprehension impairment, an intellectual disorder, a developmental disorder, stress, anxiety, Williams syndrome, Prader Willi syndrome, Smith Magenis syndrome, Bardet Biedl syndrome, or Down's syndrome or other neurological disorder.

The input message may be a spoken message or a written message. In an embodiment, the input message is a spoken message. In an embodiment, the input message is a written message.

In some embodiments, the method further comprises one or more of (vii) generating a textual message relating to the input text and representing an output message to be displayed to a user; (viii) modifying at least one character of the textual message in a manner expected to optimize the user's understanding and/or recall of the textual message as seen on a visual display; and (ix) displaying the modified textual message on a display device. In an embodiment, the method comprises (vii). In an embodiment, the method comprises (viii). In an embodiment, the method comprises (ix).

In some embodiments, generating the patterned musical message from the timed text input and the plurality of melody segments based at least in part on the plurality of matching metrics comprises accessing pitch information and timing information about a note in a melody segment; and/or setting a pitch and a timing for a phoneme in the timed text input based on the pitch information and the timing information. In an embodiment, the output device is at least one of a virtual reality device, an augmented reality headset device, and a smart speaker executing a digital personal assistant.

In another aspect, the present disclosure features a real time musical translation device (RETM) comprising: an input interface; a processor; an audio output component; and a memory communicatively coupled to the processor and comprising instructions that when executed by the processor cause the processor to perform one or more of the following tasks: (i) receive text input from the input interface; (ii) determine, for the text input, a plurality of spoken pause lengths and a plurality of spoken phoneme lengths; (iii) map the plurality of spoken pause lengths to a respective plurality of sung pause lengths; (iv) map the plurality of spoken phoneme lengths to a respective plurality of sung phoneme lengths; (v) generate, from the plurality of sung pause lengths and the plurality of sung phoneme lengths, a timed text input; (vi) generate a plurality of matching metrics for each of a respective plurality of portions of the timed text input against a plurality of melody segments; (vii) generate a patterned musical message from the timed text input and the plurality of melody segments based at least in part on the plurality of matching metrics; and (viii) output the patterned musical message using the audio output component.

In an embodiment, the RETM processor performs one of (i)-(viii). In an embodiment, the RETM processor performs two of (i)-(viii). In an embodiment, the RETM processor performs three of (i)-(viii). In an embodiment, the RETM processor performs four of (i)-(viii). In an embodiment, the RETM processor performs five of (i)-(viii). In an embodiment, the RETM processor performs six of (i)-(viii). In an embodiment, the RETM processor performs seven of (i)-(viii). In an embodiment, the RETM processor performs each of (i)-(viii).

In an embodiment, the RETM further comprises a display device. The processor may be further configured to provide to a user a visual image on the display device. In an embodiment, the visual image relates to the patterned musical message. In an embodiment, the display device is incorporated into the output device.

In an embodiment, the RETM processor is further configured to perform one or more of the following tasks: (ix) generate a textual message relating to the input text and representing an output message to be displayed to a user; (x) modify at least one character of the textual message in a manner expected to optimize the user's understanding and/or recall of the textual message; and (xi) display the modified textual message on the display device. In an embodiment, the RETM processor performs one of (ix)-(xi). In an embodiment, the RETM processor performs two of (ix)-(xi). In an embodiment, the RETM processor performs each of (ix)-(xi).

The RETM processor may be configured to modify the at least one character of the textual message in the manner expected to optimize the user's understanding and/or recollection of the textual message by at least one of removing or modifying at least one segment of the at least one character, modifying a size of the at least one character relative to other characters in the textual message, and modifying a display time of the at least one character relative to the other characters in the textual message.

In an embodiment, the RETM is presented to a user having a cognitive impairment, a behavioral impairment, or a learning impairment. In an embodiment, the user has at least one of autism spectrum disorder, attention deficit disorder, attention deficit hyperactivity disorder, aphasia, dementia, dyslexia, dysphasia, apraxia, stroke, traumatic brain injury, schizophrenia, schizoaffective disorder, depression, bipolar disorder, post-traumatic stress disorder, Alzheimer's disease, Parkinson's disease, age-related cognitive impairment, Down's syndrome, Smith Magenis syndrome, Bardet Biedl syndrome, anxiety, stress, and a language comprehension impairment.

In another aspect, the present disclosure features a method of transforming textual input to a musical score for improving a cognitive process in a user comprising providing the user with access to a real-time musical translation device (RETM), wherein the RETM comprises an input interface; a processor; an audio output component; and a memory communicatively coupled to the processor and comprising instructions that when executed by the processor cause the processor to perform one or more of the following tasks: (i) receive text input from the input interface; (ii) determine, for the text input, a plurality of spoken pause lengths and a plurality of spoken phoneme lengths; (iii) map the plurality of spoken pause lengths to a respective plurality of sung pause lengths; (iv) map the plurality of spoken phoneme lengths to a respective plurality of sung phoneme lengths; (v) generate, from the plurality of sung pause lengths and the plurality of sung phoneme lengths, a timed text input; (vi) generate a plurality of matching metrics for each of a respective plurality of portions of the timed text input against a plurality of melody segments; (viii) generate a patterned musical message from the timed text input and the plurality of melody segments based at least in part on the plurality of matching metrics; and (ix) output the patterned musical message to the user using the audio output component.

In an embodiment, the RETM processor performs one of (i)-(viii). In an embodiment, the RETM processor performs two of (i)-(viii). In an embodiment, the RETM processor performs three of (i)-(viii). In an embodiment, the RETM processor performs four of (i)-(viii). In an embodiment, the RETM processor performs five of (i)-(viii). In an embodiment, the RETM processor performs six of (i)-(viii). In an embodiment, the RETM processor performs seven of (i)-(viii). In an embodiment, the RETM processor performs each of (i)-(viii).

In an embodiment, the patterned musical message is expected to optimize a user's understanding of the input message. In an embodiment, the method further comprises providing to the user a visual image relating to the patterned musical message. In an embodiment, the user has a cognitive impairment, a behavioral impairment, or a learning impairment. In an embodiment, the user has at least one of autism spectrum disorder, attention deficit disorder, attention deficit hyperactivity disorder, aphasia, dementia, dyslexia, dysphasia, apraxia, stroke, traumatic brain injury, schizophrenia, schizoaffective disorder, depression, bipolar disorder, post-traumatic stress disorder, Alzheimer's disease, Parkinson's disease, age-related cognitive impairment, Down's syndrome, Smith Magenis syndrome, Bardet Biedl syndrome, anxiety, stress, and a language comprehension impairment or another neurological disorder.

In an embodiment, the user has dyslexia, and the RETM is configured to present a series of predefined tests and/or tasks to the user in order to evaluate and improve comprehension. In an embodiment, the user has had a stroke, and the RETM is configured to evaluate the user's ability to respond and show improved comprehension to the patterned musical message and/or shows an improved ability to speak or otherwise communicate. In an embodiment, the user has been diagnosed with autism spectrum disorder, and the RETM is configured to evaluate the user's ability to respond to the patterned musical message. In an embodiment, the patterned message is presented to the user for at least one of enhancing comprehension, improving communication, and increasing social interaction.

In an embodiment, the method further comprises one or more of: (x) tracking a performance of the user over successive uses of the RETM; and (xi) determining, from the performance of the user, a measure of improvement of the user in at least one area. In an embodiment, the method comprises (x). In an embodiment, the method comprises (xi).

In yet another aspect, the present disclosure features a method of determining a melody track in a music file, or a close derivative of the melody track, comprising one or more of (i) accessing a plurality of tracks in the music file; (ii) scoring each of the plurality of tracks according a plurality of melody heuristics; and (iii) identifying a melody track from among the plurality of tracks based at least in part on the plurality of melody heuristics for the melody track. In an embodiment, the method comprises (i). In an embodiment, the method comprises (ii). In an embodiment, the method comprises (iii). In an embodiment, the plurality of melody heuristics comprises at least one of a motion of the melody track, a number of notes in the melody track, a rhythmic density of the melody track, an entropy the melody track, and a pitch/height ambitus of melody track.

The details of one or more embodiments of the invention are set forth herein. Other features, objects, and advantages of the invention will be apparent from the Detailed Description, the Figures, the Examples, and the Claims.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of a particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the figures:

DETAILED DESCRIPTION

Real-Time Musical Translation Device

Figure 1:
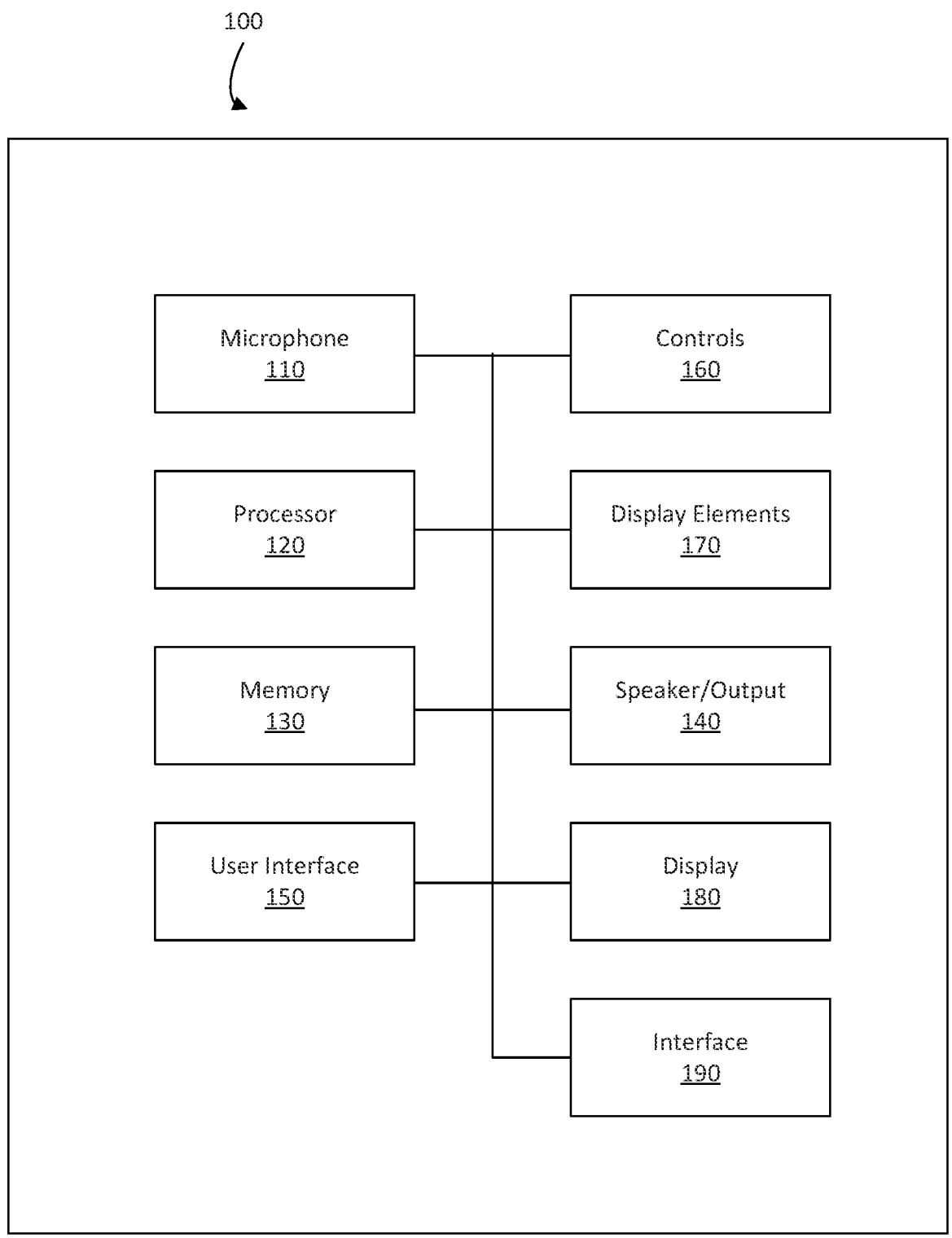
FIG. 1 is a functional block diagram of a real-time musical translation device (RETM) according to one embodiment.

A block diagram of an exemplary real-time musical translation device (RETM) 100 is shown in FIG. 1. The RETM 100 may include a microphone 110 for receiving an audio input (e.g., spoken information) from a user, and may also be configured to receive voice commands for operating the RETM 100 from the user via the microphone. A processor 120 and a memory 130 are in communication with each other and the microphone to receive, process through selected algorithms and code, and/or store the audio input or information or signals derived therefrom, and ultimately to generate the patterned musical message. A user interface 150, along with controls 160 and display elements 170, allow a user to interact with the RETM 100 (e.g., by picking a song to use as a basis for generating the patterned musical message). A speaker or other output 140 may act as a transducer (i.e., convert the patterned musical message to an audio signal) or may provide the patterned musical message device to another device (e.g, headphones or an external speaker). Optionally, a display device 180 may display visual and/or textual information designed to reinforce and/or complement the patterned musical message. An interface 190 allows the RETM 100 to communicate with other devices, including through local connection (e.g., Bluetooth) or through a LAN or WAN (e.g., the Internet).

The microphone 110 may be integrated into the RETM 100, or may be an external and/or separately connectable microphone, and may have any suitable design or response characteristics. For example, the microphone 110 may be a large diaphragm condenser microphone, a small diaphragm condenser microphone, a dynamic microphone, a bass microphone, a ribbon microphone, a multi-pattern microphone, a USB microphone, or a boundary microphone. In some examples, more than one microphone may be deployed in an array. In some embodiments, the microphone 110 may not be provided (or if present may not be used), with audio input received from an audio line in (e.g., AUX input), or via a wired or wireless connection (e.g., Bluetooth) to another device.

The processor 120 and/or other components may include functionality or hardware for enhancing and processing audio signals, including, for example, signal amplification, analog-to-digital conversion/digital audio sampling, echo cancellation, audio mastering, or other audio processing, etc., which may be applied to input from the microphone 110 and/or output to the speaker 140 of the RETM 100. As discussed in more detail below, the RETM 100 may employ pitch- and time-shifting on the audio input, with reference to a score and/or one or more rules, in order to convert a spoken message into the patterned musical message.

The memory 130 is non-volatile and non-transitory and may store executable code for an operating system that, when executed by the processor 120, provides an application layer (or user space), libraries (also referred to herein as "application programming interfaces" or "APIs") and a kernel. The memory 130 also stores executable code for various applications, including the processes and sub-processes described here. Other applications may include, but are not limited to, a web browser, email client, calendar application, etc. The memory may also store various text files and audio files, such as, but not limited to, text to be converted to a patterned musical message; a score or other notation, or rules, for the patterned musical message; raw or processed audio captured from the microphone 110; the patterned musical message itself; and user profiles or preferences. Melodies may be selected and culled according to their suitability for optimal text acceptance. This selection may be made by a human (e.g., the user or an instructor) and/or automatically by the RETM or other computing device, such as by using a heuristic algorithm.

The source or original score may be modified to optimally become aligned with voice and/or text, leading to the generated score, which, includes the vocal line, is presented by the synthesized voice and presents the text as lyrics. The generated score, i.e. the musical output of the RETM, may include pitch and duration information for each note and rest in the score, as well as information about the structure of the composition represented by the generated score, including any repeated passages, key and time signature, and timestamps of important motives. The generated score may also include information regarding other parts of the composition not included in the patterned musical message. The score may include backing track information, or may provide a link to a prerecorded backing track and/or accompaniment. For example, the RETM 100 may perform a backing track along with the patterned musical message, such as by simulating drums, piano, backing vocals, or other aspects of the composition or its performance. In some embodiments, the backing track may be one or more short segments that can be looped for the duration of the patterned musical message. In some examples, the score is stored and presented according to a technical standard for describing event messages, such as the Musical Instrument Digital Interface (MIDI) standard. Data in the score may specify the instructions for music, including a note's notation, pitch, velocity, vibrato, and timing/tempo information.

A user interface 150 may allow the user to interact with the RETM 100. For example, the user (e.g., instructor or student) may use user interface 150 to select a song or genre used in generating the patterned musical message, or to display text that the user may read to provide the audio input. Other controls 160 may also be provided, such a physical or virtual buttons, capacitive sensors, switches, or the like, for controlling the state and function of the RETM 100. Similarly, display elements 170 may include LED lights or other indicators suitable for indicating information about the state or function of the RETM 100, including, for example, whether the RETM 100 is powered on, whether it is currently receiving audio input or playing back the patterned musical message. Such information may also be conveyed by the user interface 150. Tones or other audible signals may also be generated by the RETM 100 to indicate such state changes.

The user interface 150 allows one or more users to select a musical pattern and/or ruleset as discussed herein. In some examples, different users may have different abilities to control the operation of the RETM 100 using the user interface 150. For example, whereas a first user (e.g., an instructor) may be allowed to select a disorder, a genre, and/or a song, a second user (e.g., a student) may be constrained to choosing a particular song within a genre and/or set of songs of songs classified for a particular disorder by the first user or otherwise. In this manner, a first user can exercise musical preferences within a subset of musical selections useful for treating a second user. In an embodiment, a first user can exercise musical preferences within a subset of musical selection useful for treating a plurality of users, such as a second user, a third user, or a fourth user.

In some examples, the user may interact with the RETM 100 using other interfaces in addition to, or in place of, user interface 150. For example, the RETM 100 may allow for voice control of the device ("use 'rock & roll'"), and may employ one or more wake-words allowing the user to indicate that the RETM 100 should prepare to receive such a voice command.

The display 180 may also be provided, either separately or as part of the user interface 150, for displaying visual or textual information that reinforces and/or complements the information content of the text or voice or spoken words of the patterned musical message. In some embodiments, the display 180 may be presented on an immersive device such as a virtual reality (VR) or augmented reality (AR) headset.

The interface 190 allows the RETM 100 to communicate with other devices and systems. In some embodiments, the RETM 100 has a pre-stored set of data (e.g., scores and backing tracks); other embodiments, the RETM 100 communicates with other devices or systems in real time to process audio and/or generate the patterned musical message. Communications can be achieved via one or more networks, such as, but are not limited to, one or more of WiMax, a Local Area Network (LAN), Wireless Local Area Network (WLAN), a Personal area network (PAN), a Campus area network (CAN), a Metropolitan area network (MAN), a Wide area network (WAN), a Wireless wide area network (WWAN), enabled with technologies such as, by way of example, Global System for Mobile Communications (GSM), Personal Communications Service (PCS), Digital Advanced Mobile Phone Service (D-Amps), Bluetooth, Wi-Fi, Fixed Wireless Data, 2G, 2.5G, 3G, 4G, IMT-Advanced, pre-4G, 3G LTE, 3GPP LTE, LTE Advanced, mobile WiMax, WiMax 2, WirelessMAN-Advanced networks, enhanced data rates for GSM evolution (EDGE), General packet radio service (GPRS), enhanced GPRS, iBurst, UMTS, HSPDA, HSUPA, HSPA, UMTS-TDD, 1×RTT, EV-DO, messaging protocols such as, TCP/IP, SMS, MMS, extensible messaging and presence protocol (XMPP), real time messaging protocol (RTMP), instant messaging and presence protocol (IMPP), instant messaging, USSD, IRC, or any other wireless data networks or messaging protocols.

Figure 2A:
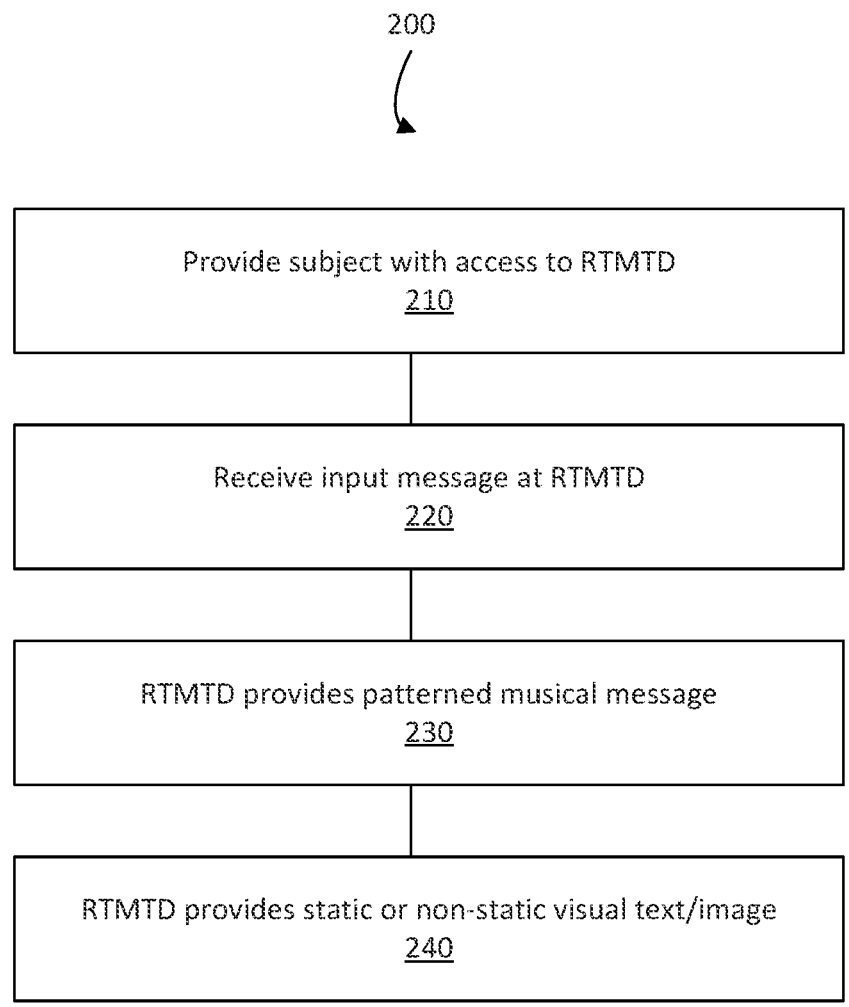
FIG. 2A depicts a process for operating the application and/or a device according to one embodiment.

A method 200 of transposing spoken or textual input to a patterned musical message is shown in FIG. 2A.

At step 202, the method begins.

At step 204, text input is received. Text input may be received, for example, by accessing a text file or other computer file such as an image or photo, in which the text is stored. The text may be formatted or unformatted. The text may be received via a wired or wireless connection over a network, or may be provided on a memory disk. In other embodiments, the text may be typed or copy-and-pasted directly into a device by a user. In still other embodiments, the text may be obtained by capturing an image of text and performing optical character recognition (OCR) on the image. The text may be arranged into sentences, paragraphs, and/or larger subunits of a larger work.

At step 206, the text input is converted into a phonemic representation, as can be represented by any standard format such as ARPABET, IPA or SAMPA. This may be accomplished, in whole or in part, using free or open source software, such as Phonemizer, and/or the Festival Speech Synthesis System developed and maintained by the Centre for Speech Technology Research at the University of Edinburgh. However, in addition certain phonemes in certain conditions (e.g., surrounded by other phonemes) are to be modified so as to be better comprehended as song. The phonemic content may be deduced by a lookup table mapping (spoken phoneme, spoken phoneme surroundings) to (sung phoneme). In some cases the entire preceding or consequent phoneme is taken into account when determining a given phoneme, while in other cases only the onset or end of the phoneme is considered.

In some examples, a series of filters may be applied to the text input to standardize or optimize the text input. For example, filters may be applied to convert abbreviations, currency signs, and other standard shorthand to text more suited for conversion to speech.

At step 208, a plurality of spoken pause lengths and a plurality of spoken phoneme lengths are determined for the text input. The length of the pauses and the phonemes represented in the text input may be determined with the help of open source software or other sources of information regarding the prosodic, syntactic, and semantic features of the text or voice. The process may involve a lookup table that synthesizes duration information about phonemes and pauses between syllables, words, sentences, and other units from other sources which describe normal speech. In some examples, the spoken length of phonemes may be determined and/or categorized according to their position in a larger syntactic unit (e.g., a word or sentence), their part of speech, or their meaning. In some examples, a dictionary-like reference may provide a phoneme length for specific phonemes and degrees of accent. For example, some phonemes may be categorized as having a phoneme length of less than 0.1 seconds, less than 0.2 seconds, less than 0.3 seconds, less than 0.4 seconds, or less than 1.0 seconds. Similarly, some pauses may be categorized according to their length during natural spoken speech, based upon their position within the text or a subunit thereof, the nature of phonemes and/or punctuation nearby in the text; or other factors.

At step 210, the plurality of spoken pause lengths is mapped to a respective plurality of sung pause lengths. For example, a Level 1 spoken pause (as discussed above) in spoken text may be mapped to a Level 1 sung pause, which may have a longer or shorter duration that the correspond spoken pause. In some examples, any Level 1 spoken pause may be mapped to an acceptable range of Level 1 sung pauses. For example, a Level 1 spoken pause may be mapped to a range of Level 1 sung pauses of between 0.015 to 0.08 seconds or between 0.03 to 0.06 seconds. Similarly, a Level 2 spoken pause may be mapped to a sung pause of between 0.02 to 0.12 seconds or between 0.035 to 0.1 seconds. A Level 3 spoken pause may be mapped to a sung pause of between 0.05 to 0.5 seconds or between 0.1 to 0.3 seconds; and a Level 4 spoken pause may be mapped to a sung pause of between 0.3 to 1.5 seconds or between 0.5 to 1.0 seconds.

At step 212, the plurality of spoken phoneme lengths is mapped to a respective plurality of sung phoneme lengths. The mapping may represent, for a spoken phoneme of a given length, a range of optimal lengths for the phoneme when sung. In some examples, a lookup table may be used, such as the following:

| Spoken Phoneme Length | Optimal Sung Phoneme Length |
| --- | --- |
| <0.1 seconds | 0.1 to 0.5 seconds |
| <0.2 seconds | 0.3 to 0.7 seconds |
| <0.3 seconds | 0.35 to 0.8 seconds |
| >=0.3 seconds | 0.4 to 0.9 seconds |

In another example, a broader range of values may be used:

| Spoken Phoneme Length | Optimal Sung Phoneme Length |
| --- | --- |
| <0.1 seconds | 0.05 to 0.7 seconds |
| <0.2 seconds | 0.2 to 0.9 seconds |
| <0.3 seconds | 0.3 to 1.0 seconds |
| >=0.3 seconds | 0.35 to 1.5 seconds |

It will be appreciated that the plurality of spoken pause lengths and the plurality of spoken phoneme lengths applied in steps 210 and 212, respectively, may be determined with reference to one or more parameters. Those parameters may include optimal breaks between sentences, optimal tempo, optimal time signature, optimal pitch range, and optimal length of phonemes, where optimality is measured with respect to facilitating comprehension and/or recollection. In some cases, a number of these factors may be applied, possibly with relative weights, in mapping the plurality of spoken pause lengths and the plurality of spoken phoneme lengths.

Certain constraints may be imposed on the plurality of spoken pause lengths and the plurality of spoken phoneme lengths. In particular, spoken pause lengths and spoken phoneme lengths determined in the previous steps may be adjusted according to certain constraints in order to optimize comprehension and musicality. The constraints may be set based on the frequency/commonality of the word, or on its position within a sentence or clause, such as a "stop" word. For example, a constraint may be enforced that all phonemes in stop words must have a length of <=0.6 seconds. A stop word, as used herein, may be natural language words which have very little meaning, such as "and", "the", "a", "an", and similar words. Similarly, a constraint may be enforced that all phonemes in words that do not appear in the list of the most frequent 10,000 words must have a length of >=0.2 seconds. In another example, a constraint may be enforced that a pause after a stop word that does not end a sentence cannot be greater than 0.3 seconds.

At step 214, a timed text input is generated from the plurality of sung pause lengths and the plurality of sung phoneme lengths. In particular, each phoneme and pause in the text input is stored in association with its respective optimal timing (i.e., length) information determined in the previous steps. The timed text input (i.e., the text input and associated timing information) may be stored in an array, a record, and/or a file in a suitable format. In one example, a given phoneme in the timed text input may be stored as a record along with the lower and upper optimal length values, such as the following:

{"dh-ax-s"", 0.1, 0.5} where the phoneme "dh-ax-s" (an ARPABET representation of the pronunciation of the word "this") has been assigned an optimal sung phoneme length of between 0.1 and 0.5 seconds.

At step 216, a plurality of matching metrics is generated for each of a respective plurality of portions of the timed text input against a plurality of melody segments. The plurality of melody segments may be accessed in a MIDI file or other format. In addition to a melody line, a musical score or other information for providing an accompaniment to the melody may be accessed. For example, a stored backing track may be accessed and prepared to be played out in synchronization with the melody segments as described in later steps.

In particular, the timed text input may be broken up into portions representing sentences, paragraphs of text, or other units. Each portion is then compared to a plurality of melody segments, with each melody segment being a musical line having its own pitch and timing information.

Each melody segment may be thought of as the definition of a song, melody, or portion thereof, and may comprise a score as discussed above. For example, the melody segment may include, for each note in the melody, a number of syllables associated with the note, a duration of the note, a pitch of the note, and any other timing information for the note (including any rests before or after the note). While reference is made to a "pitch" of the note, it will be appreciated that the pitch may not be an absolute pitch (i.e., 440 Hz), but rather may be a relative pitch as defined by its position within the entire melody. For example, the melody segment may indicate that a particular note within the melody should be shifted to note with integer pitch 69 (equivalent to the letter note "A" in the fourth octave), but if it is deemed impossible to pronounce an A in fourth octave, the entire melody may be shifted downwards, so that each subsequent note it lowered by the same amount.

Other methods of musical corrective action may also be undertaken to enhance comprehension of the generated audio output. For example, the pitch (and all subsequent pitches) may be shifted to the appropriate note as an audio input message (i.e., the user's speaking voice), or some number of pitches above or below that original note, with the goal of sounding as natural as possible. In some example, the RETM may attempt to shift the pitches of the song by a particular number of semitones based on the nature of the disorder, the original pitch of the speaker's voice, or based on some determination that performance in that octave will be aesthetically pleasing.

For each comparison of a portion of a timed text input to a melody segment, a matching metric is generated representing the "fit" of the portion of the timed text input to the corresponding melody segment. For example, a melody segment with notes whose timing aligns relatively closely with the timing information of the corresponding portion of the timed text input may be assigned a higher matching metric than a melody segment that does not align as well timing-wise. A melody segment having the highest matching metric for a portion of the timed text input may be selected for mapping onto by the portion of the timed text input in subsequent steps.

The melody segments may be selected based on their harmonic and rhythmic profiles, such as their tonic or dominant scale qualities over the course of the melody. A subset of available melody segments may be chosen as candidates for a particular timed text input based on similar or complimentary musical qualities to ensure melodic coherence and appeal. In some examples, a user (e.g., an instructor) may be permitted to select a tonal quality (e.g., major or minor key) and/or tempo using a graphical or voice interface.

In some embodiments, a dynamic programming algorithm may be employed to determine which phonemes or words within the timed text input are to be matched with which melody segments or notes thereof. The algorithm may take into account linguistic features as well as their integration with musical features. For example, the algorithm may apply the timed text input to a melody segment such that a point of repose in the music (e.g., a perfect authentic cadence, commonly written as a "PAC") is reached where there is a significant syntactic break. As another example, the algorithm may prevent breaking up stop words such as "the" with their following constituents; may favor harmonic tension following the syntax of the text. As another example, the algorithm may favor a longer duration for words assumed to be more rare and/or harder to hear in order to optimize comprehension and musicality.

A score function may be used by the dynamic programming algorithm in some embodiments for purposes of generating the matching metric between the portion of the timed text input and melody segment. The score function may weigh individual criteria, and the weights may be automatically set, dynamically adjustable, or adjustable by a user. In one example, one criterion may be the difference between the sung phoneme length(s) and the constraints imposed by the corresponding melody segment. In some embodiments, this length criterion may account for 50% of the score function. The length criterion may take into account the fit of the melody segment to the sung phoneme length as determined in steps 240 and 250 (80%), as well as syntactic/stop word analysis (10%), and word rarity (10%).

Another criterion taken into account in the scoring metric may be the degree to which pauses occur between complete clauses (30%). This may be determined by using a phrase structure grammar parser to measure the minimum depth of a phrase structure parsing of the sentence at which two sequential elements in the same chunking at that level are divided by the melody. If the depth is greater than or equal to some constant determined by the phrase structure grammar parser used (e.g., 4 for the open-source benepar parser), such a placement of the pause may be penalized.

Another criterion taken into account in the scoring metric may be the existence of unresolved tension only where the clause is incomplete (20%). A melody segment may be penalized where it causes a sentence or independent clause to end on the dominant or leading tone, or on a note with a duration of <1 beat.

In some examples, where none of the melody segment fit the portion of the timed text or voice input to a suitable degree, the timed text or voice input may be split into two or more subportions and the process repeated in an effort to locate one or a series of melody segments that fits each subportion of timed text or voice input to an acceptable degree.

At step 280, a patterned musical message is generated from the timed text or voice input and the plurality of melody segments based at least in part on the plurality of matching metrics. For example, each phoneme of the timed text input may be pitch shifted according the corresponding notes(s) in the melody segment. The phoneme is set to the melody using phonetic transcription codes, such as ARPABET. The patterned musical message, with or without accompaniment, may then be output as a sound file, such as a .WAV or .MP3 file suitable for output by a playback device. The patterned musical message may be encoded with timestamps indicating a relative or absolute time at which each portion (e.g., note) of the melody is to be output.

At step 218, after or concurrent with output of the patterned musical message, visual or textual information may optionally be presented to reinforce or complement the patterned musical message. For example, the RETM may cause to be displayed, on a display screen or on-head display (such as a virtual reality or augmented reality display-enabled headset), the wording or imaging reflective of wording currently being output as part of the patterned musical message. In some embodiments, text corresponding to the currently played phoneme or the larger unit in which it is contained (e.g., word or sentence) may be highlighted or otherwise visually emphasized in order to enhance comprehension or recall. Identification of the currently played phoneme may be performed with reference to a timestamp associated a respectively timestamp associated with each phoneme in the patterned musical message.

Figure 5:
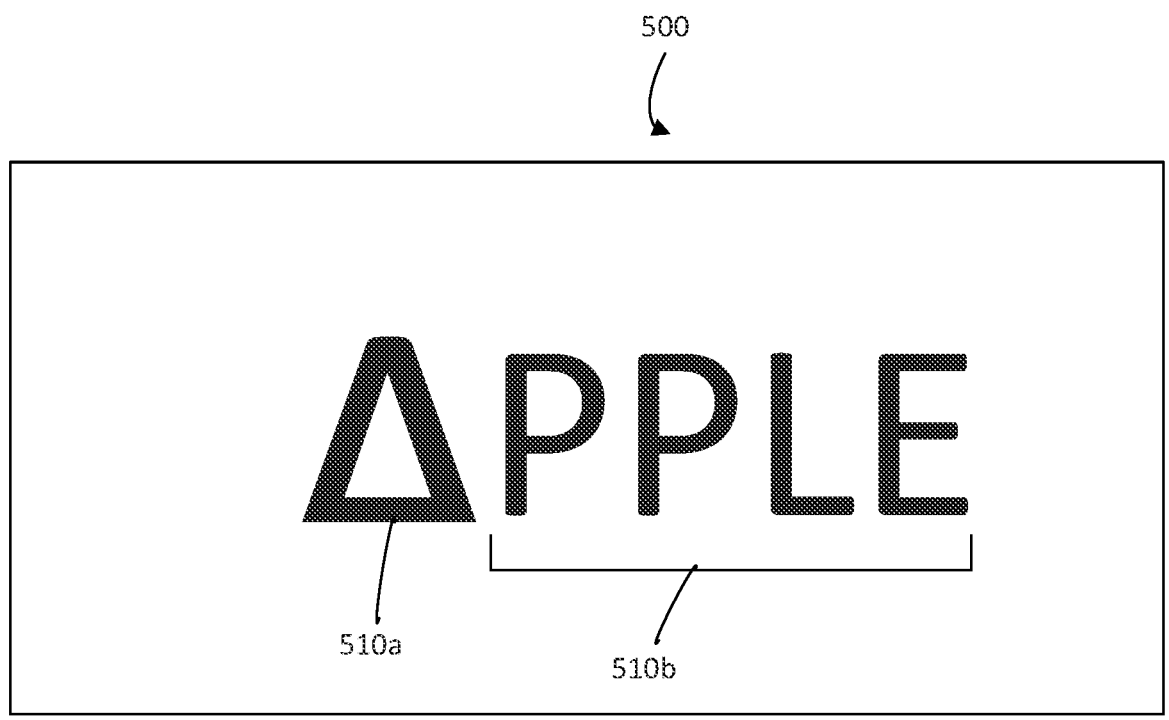
FIG. 5 depicts an exemplary user interface according to one embodiment.

In some examples, characters in text being displayed may have their appearance modified in a way intended to optimize cognition and/or recall. An example screenshot 500 is shown in FIG. 5. In that example, the word "APPLE" is shown, but with the letter "A" (shown at 510a) being modified, having lowered and extended the horizontal feature of the letter. The remaining letters 510b are unchanged in appearance. Such and similar modified, and partial forms of any letters may be stored in association with one or more disorders, and displayed only when appropriate to treat such disorders. Other examples of modifications to characters include size, font face, movement, timing, or location relative to the other characters. In other examples, visual representations of the word (e.g., a picture of an apple when the word "apple" is sung in the patterned musical message) may be shown on the display. In some embodiments, virtual reality or augmented reality elements may be generated and displayed.

At step 220, the method ends.

According to some embodiments, the method 200 may be performed using a RETM (e.g., RETM 100 as seen in FIG. 1). The RETM may be a dedicated device, or may be the user's mobile device executing special-programmed software. In some examples, the user may be undergoing treatment with selected pharmacotherapeutics or behavioral treatments, or the user may be provided with or otherwise directed to use the RETM in combination with a drug or other therapeutic treatment intended to treat a disorder.

In some embodiments as described above, the input message may be textual input received from the user via a physical or virtual keyboard, or may be accessed in a text file or other file, or over a network. In other embodiments, the input text may be provided or derived from spoken or textual input by the user. In one example, the input message may be speech captured by a microphone (e.g., microphone 110) and stored in a memory (memory 130). In some examples, the intermediate step of parsing the input message spoken by the user into components parts of speech may be performed as a precursor to or in conjunction with step 206 as discussed above. In other examples, parsing the spoken input into text may be modified or omitted, and the waveform of the input message itself may simply be pitch-shifted according to certain rules and/or constraints as discussed below. In either case, it will be appreciated that a user's spoken input message may be mapped to and output as a melody in real-time or near-real-time as discussed herein.

Figure 2B:
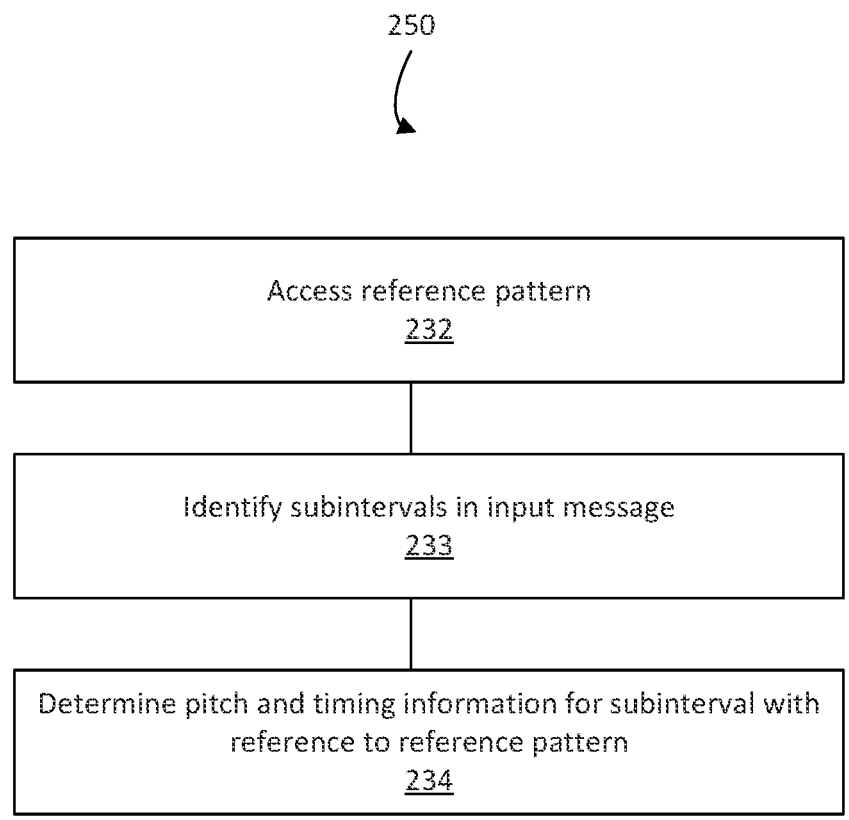
FIG. 2B depicts a process for operating the application and/or a device according to one embodiment.

An example block diagram for processing a variety of input messages is shown in FIG. 2B. For example, text input 254 may be received from a user and filtered and standardized at processing block 258, converted to phonemes at processing block 260, and used to generate a patterned musical message at processing block 262 based on a provided melody 266, according to the techniques described herein. In another example, spoken input is received at a microphone 252 and provided to an audio interface 256. Speech captured by the microphone 252 may undergo any number of pre-processing steps, including high pass, low pass, notch, band pass or parametric filtering, compression, expansion, clipping, limiting, gating, equalization, spatialisation, de-essing, de-hissing, and de-crackling. In some embodiments, the audio input may be converted to text (e.g., for display on a device) using speech-to-text language processing techniques aimed at enhancing language comprehension.

The spoken input may then be converted to text using voice/speech recognition algorithms and processed in the same manner as the text 254 in processing blocks 258, 260, and 262.

In another embodiment, the spoken input may be directly parsed at processing block 264 without the intermediate step of converting to text. The audio input message may be parsed or processed in a number of ways at processing block 264. In some examples, waveform analysis allows the system to delineate individual syllables or other distinct sounds where they are separated by (even brief) silence as revealed in the waveform, which represents the audio input message as a function of amplitude over time. In these embodiments, syllables may be tagged by either storing them separately or by storing a time code at which they occur in the audio input message. Other techniques may be used to identify other parts of speech such as phonemes, words, consonants, or vowels, which may be detected through the use of language recognition software and dictionary lookups.

In some embodiments, the system may be configured to operate in a real-time mode; that is, audio input received at the microphone, or textual input received by the system, is processed and converted to a portion of the patterned musical message nearly instantaneously, or with a lag so minimal that it is either not noticeable at all or is slight enough so as not to be distracting. Input may be buffered, and the steps 202-220 may be performed repeatedly on any buffered input, to achieve real-time or near-real time processing. In these embodiments, the most recent syllable of the audio input message may continuously be detected and immediately converted to a portion of the patterned musical message. In other embodiments, the system may buffer two or more syllables to be processed. In some embodiments, the time between receiving the audio or text input message and outputting the patterned musical message should be vanishingly small so as to be virtually unnoticeable to the user. In some examples, the delay may be less than 2 seconds, and in further examples, the delay may be less than 0.5 seconds. In some examples, the delay may be less than 5 seconds, or less than 10 seconds. While the translation of spoken voice or text into song using the RETM may lengthen its presentation and thus lead to the termination of the song more than 10 seconds after the speaker finishes speaking in the case of a long utterance, the flow of song will be smooth and uninterrupted and will begin shortly after the speaker begins speaking.

Figure 3:
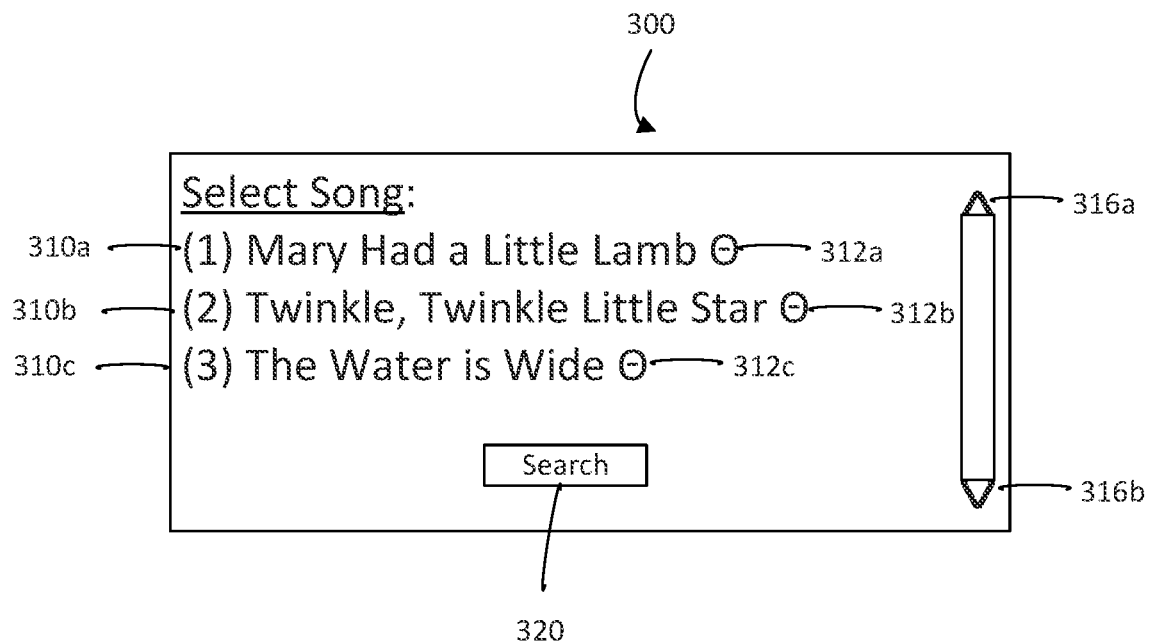
FIG. 3 depicts an exemplary user interface according to one embodiment.

An exemplary user interface 300 for selecting a particular genre is shown in FIG. 3. The user interface 300 includes a list of selectable genres 310a-c, which may be selected by touching or otherwise interacting with the user interface. Additional information about the genre may be displayed by clicking on the corresponding information indicator 312a-c next to each genre. Controls 316a,b allow the user to scroll up and down or otherwise navigate the list, and a search functionality may be provided by interacting with control element 320. The search functionality may allow the user to search for available genres.

It will be appreciated that a broad selection of melodies and melody segments will facilitate optimal matching of the time text input to melody segments (e.g., in steps 270 and 280 discussed above), and that such a broader selection also increases user engagement and enjoyment. It will also be appreciated that identifying melodies for inclusion in the pool of available options may be time-intensive, since a desired melody may be provided in available music alongside rhythm and other tracks. For example, a Musical Instrument Digital Interface (MIDI) music file for a particular song may contain a melody track along with other instrumentation (e.g., a simulated drum beat or bass line), and one or more harmony lines. There is therefore an advantage to providing an automatic method of identifying a melody among a collection of tracks forming a musical piece, in order to add additional melody segments to the collection available for matching to the timed text input as discussed above. This is accomplished by detecting one or more characteristics of a melody within a given musical line and scoring the musical line according to its likelihood of being a melody.

Figure 4:
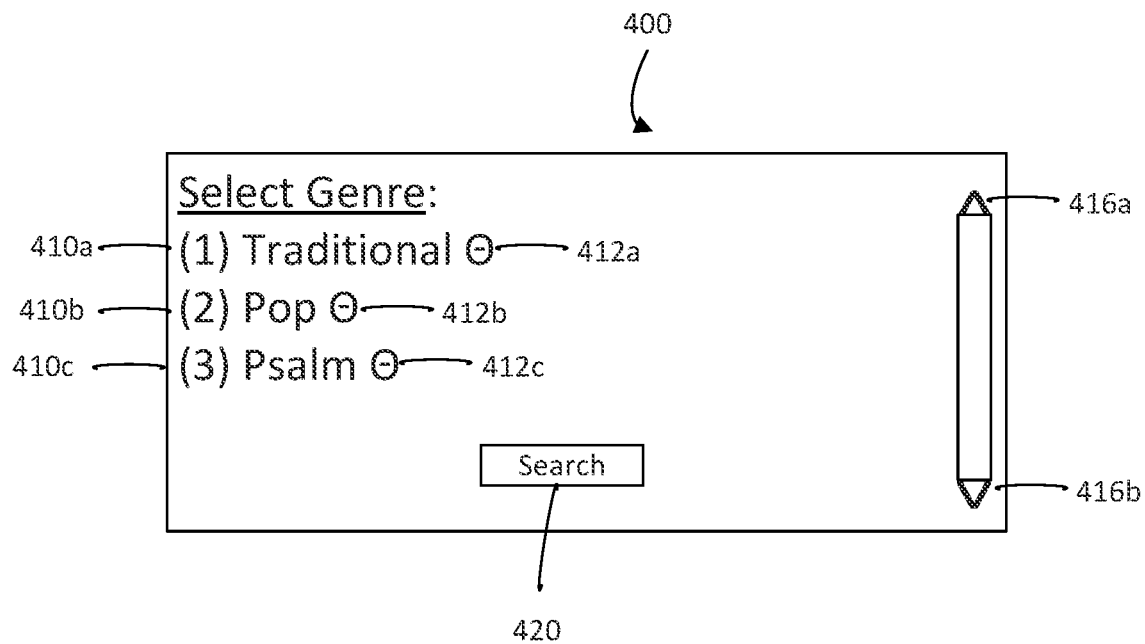
FIG. 4 depicts a process for operating the application and/or a device according to one embodiment.

A method 400 of determining a melody track in a music file is described with reference to FIG. 4.

At step 410, the method begins.

At step 420, a plurality of tracks in a music file are accessed. For example, a MIDI file, a musicXML file, abc format file or other file format, may be accessed and all of the individual lines as defined by the channels/tracks in the MIDI file will be stored and accessed. Each of these lines can be evaluated as a possible melody line.

At step 430, each of the plurality of tracks is scored according to a plurality of melody heuristics. The plurality of melody heuristics may represent typical identifying characteristics of a melody. For example, the melody heuristics may represent the amount of "motion" in the melody, the number of notes, the rhythmic density (both in a given section and throughout the piece), the entropy (both in a given section and throughout the piece), and the pitch/height ambitus of the track. The melody heuristics may score a track according to a number of specific criteria that quantify those characteristics. For example, a track may be scored according to the number of interval leaps greater than a certain amount (e.g., 7 semitones); a track with a greater number of such large jumps may be less likely to be the melody. In another example, the track may be scored according to its total number of notes; a track having more notes may be more likely to be the melody. In another example, the track may be scored according to a median number of notes with no significant rest in between them; a track with fewer rests between notes may be more likely to be the melody. In another example, the track may be scored according to a median Shannon entropy of every window of the melody between 8 and 16 notes long; a track with a higher entropy may be more likely to be the melody. In another example, the track may be scored according to a number of notes outside of a typical human singing range (e.g., notes outside of the range of MIDI pitches from 48 to 84); a track with more unsingable notes may be less likely to be the melody. Other measurements that could be used include mean, median, and standard deviation of length of note durations, note pitches, and absolute values of intervals between notes, or other mathematical operators on the contents of the MIDI file.

A subscore may be determined for each of these and other criteria, and aggregated (e.g., summed) to a melody heuristic score for the track.

At step 440, a melody track is identified from among the plurality of tracks based at least in part on the plurality of melody heuristics for the melody track. For example, after each candidate track has been scored, the track with the highest melody heuristic score may be identified as the melody track. In some examples, where more than one track has a sufficiently high melody heuristic score, the candidate melody tracks may be presented to a user graphically, or may be performed audibly, so that the user can select the desired/appropriate melody track.

At step 450, the method ends.

Figure 2C:
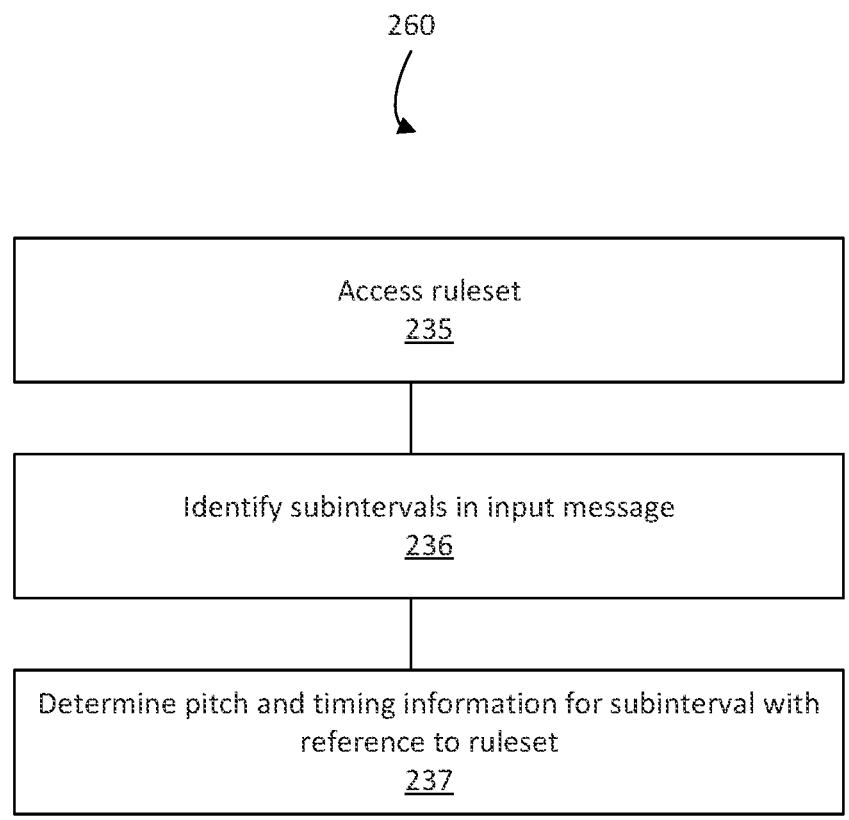
FIG. 2C depicts a process for operating the application and/or a device according to one embodiment.

After the melody track is identified, it may be split into melody segments, stored, and used to match with portions of timed text inputs as discussed above with reference to FIGS. 2A-2C.

Exemplary Computer Implementations

Processes described above are merely illustrative embodiments of systems that may be used to execute methods for transposing spoken or textual input to music. Such illustrative embodiments are not intended to limit the scope of the present invention, as any of numerous other implementations exist for performing the invention. None of the embodiments and claims set forth herein are intended to be limited to any particular implementation of transposing spoken or textual input to music, unless such claim includes a limitation explicitly reciting a particular implementation.

Processes and methods associated with various embodiments, acts thereof and various embodiments and variations of these methods and acts, individually or in combination, may be defined by computer-readable signals tangibly embodied on a computer-readable medium, for example, a non-volatile recording medium, an integrated circuit memory element, or a combination thereof. According to one embodiment, the computer-readable medium may be non-transitory in that the computer-executable instructions may be stored permanently or semi-permanently on the medium. Such signals may define instructions, for example, as part of one or more programs, that, as a result of being executed by a computer, instruct the computer to perform one or more of the methods or acts described herein, and/or various embodiments, variations and combinations thereof. Such instructions may be written in any of a plurality of programming languages, for example, Java, Python, Javascript, Visual Basic, C, C#, or C++, etc., or any of a variety of combinations thereof. The computer-readable medium on which such instructions are stored may reside on one or more of the components of a general-purpose computer described above, and may be distributed across one or more of such components.

The computer-readable medium may be transportable such that the instructions stored thereon can be loaded onto any computer system resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement the above-discussed aspects of the present invention.

The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

A computer system may be a general-purpose computer system that is programmable using a high-level computer programming language. A computer system may be also implemented using specially programmed, special purpose hardware. In a computer system there may be a processor that is typically a commercially available processor such as the Pentium class processor available from the Intel Corporation. Many other processors are available. Such a processor usually executes an operating system which may be, for example, any version of the Windows, iOS, Mac OS, or Android OS operating systems, or UNIX/LINUX available from various sources. Many other operating systems may be used. The RETM implementation may also rely on a commercially available embedded device, such as an Arduino or Raspberry Pi device.

Some aspects of the invention may be implemented as distributed application components that may be executed on a number of different types of systems coupled over a computer network. Some components may be located and executed on mobile devices, servers, tablets, or other system types. Other components of a distributed system may also be used, such as databases or other component types.

The processor and operating system together define a computer platform for which application programs in high-level programming languages are written. It should be understood that the invention is not limited to a particular computer system platform, processor, operating system, computational set of algorithms, code, or network. Further, it should be appreciated that multiple computer platform types may be used in a distributed computer system that implement various aspects of the present invention. Also, it should be apparent to those skilled in the art that the present invention is not limited to a specific programming language, computational set of algorithms, code or computer system. Further, it should be appreciated that other appropriate programming languages and other appropriate computer systems could also be used.

One or more portions of the computer system may be distributed across one or more computer systems coupled to a communications network. These computer systems also may be general-purpose computer systems. For example, various aspects of the invention may be distributed among one or more computer systems configured to provide a service (e.g., servers) to one or more client computers, or to perform an overall task as part of a distributed system. For example, various aspects of the invention may be performed on a client-server system that includes components distributed among one or more server systems that perform various functions according to various embodiments of the invention. These components may be executable, intermediate (e.g., IL) or interpreted (e.g., Java) code which communicate over a communication network (e.g., the Internet) using a communication protocol (e.g., TCP/IP). Certain aspects of the present invention may also be implemented on a cloud-based computer system (e.g., the EC2 cloud-based computing platform provided by Amazon.com), a distributed computer network including clients and servers, or any combination of systems.

It should be appreciated that the invention is not limited to executing on any particular system or group of systems. Also, it should be appreciated that the invention is not limited to any particular distributed architecture, network, or communication protocol.

Further, on each of the one or more computer systems that include one or more components of device 100, each of the components may reside in one or more locations on the system. For example, different portions of the components of device 100 may reside in different areas of memory (e.g., RAM, ROM, disk, etc.) on one or more computer systems. Each of such one or more computer systems may include, among other components, a plurality of known components such as one or more processors, a memory system, a disk storage system, one or more network interfaces, and one or more busses or other internal communication links interconnecting the various components.

Figure 6:
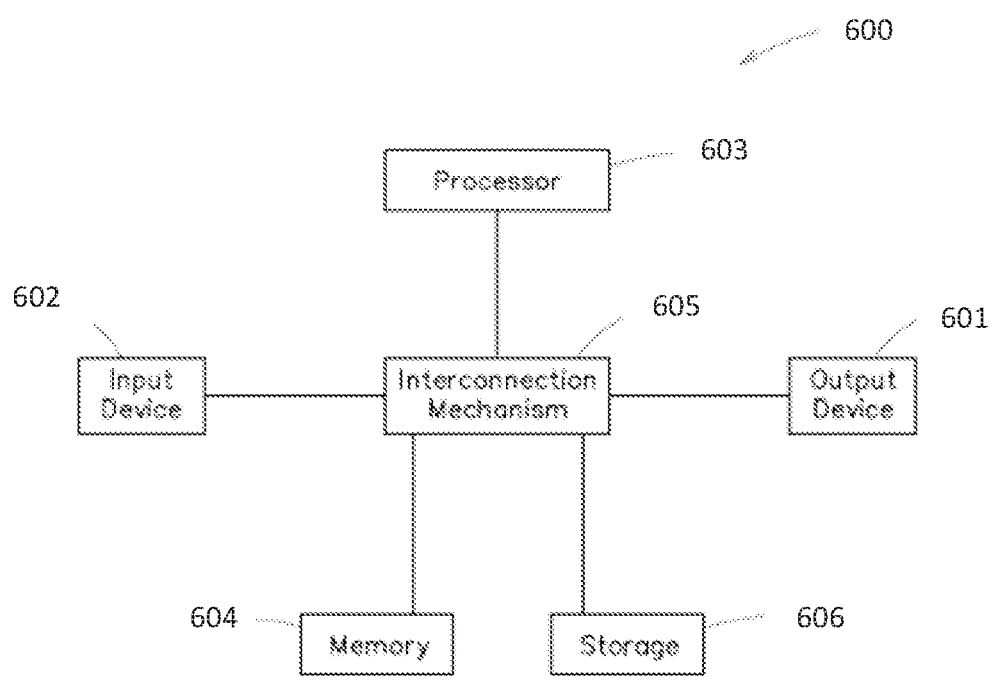
FIG. 6 shows an example computer system with which various aspects of the present disclosure may be practiced.
Figure 7:
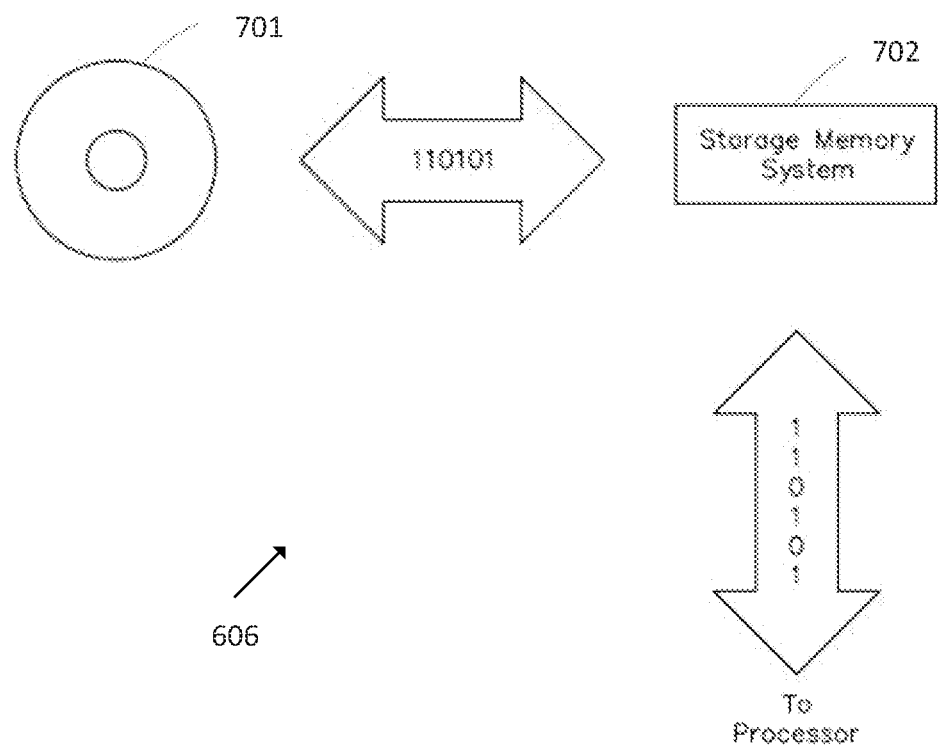
FIG. 7 shows an example storage system capable of implementing various aspects of the present disclosure.

A RETM may be implemented on a computer system described below in relation to FIGS. 6 and 7. In particular, FIG. 6 shows an example computer system 600 used to implement various aspects. FIG. 7 shows an example storage system that may be used.

System 600 is merely an illustrative embodiment of a computer system suitable for implementing various aspects of the invention. Such an illustrative embodiment is not intended to limit the scope of the invention, as any of numerous other implementations of the system, for example, are possible and are intended to fall within the scope of the invention. For example, a virtual computing platform may be used. None of the claims set forth below are intended to be limited to any particular implementation of the system unless such claim includes a limitation explicitly reciting a particular implementation.

Various embodiments according to the invention may be implemented on one or more computer systems. These computer systems may be, for example, general-purpose computers such as those based on Intel PENTIUM-type processor, Motorola PowerPC, Sun UltraSPARC, Hewlett-Packard PA-RISC processors, or any other type of processor. It should be appreciated that one or more of any type computer system may be used to partially or fully automate integration of the recited devices and systems with the other systems and services according to various embodiments of the invention. Further, the software design system may be located on a single computer or may be distributed among a plurality of computers attached by a communications network.

For example, various aspects of the invention may be implemented as specialized software executing in a general-purpose computer system 600 such as that shown in FIG. 6. The computer system 600 may include a processor 603 connected to one or more memory devices 604, such as a disk drive, memory, or other device for storing data. Memory 604 is typically used for storing programs and data during operation of the computer system 600. Components of computer system 600 may be coupled by an interconnection mechanism 605, which may include one or more busses (e.g., between components that are integrated within a same machine) and/or a network (e.g., between components that reside on separate discrete machines). The interconnection mechanism 605 enables communications (e.g., data, instructions) to be exchanged between system components of system 600. Computer system 600 also includes one or more input devices 602, for example, a keyboard, mouse, trackball, microphone, touch screen, and one or more output devices 601, for example, a printing device, display screen, and/or speaker. In addition, computer system 600 may contain one or more interfaces (not shown) that connect computer system 600 to a communication network (in addition or as an alternative to the interconnection mechanism 605).

The storage system 606, shown in greater detail in FIG. 7, typically includes a computer readable and writeable nonvolatile recording medium 701 in which signals are stored that define a program to be executed by the processor or information stored on or in the medium 701 to be processed by the program. The medium may, for example, be a disk or flash memory. Typically, in operation, the processor causes data to be read from the nonvolatile recording medium 701 into another memory 702 that allows for faster access to the information by the processor than does the medium 701. This memory 702 is typically a volatile, random access memory such as a dynamic random-access memory (DRAM) or static memory (SRAM).

Data may be located in storage system 606, as shown, or in memory system 604. The processor 603 generally manipulates the data within the integrated circuit memory 604, 602 and then copies the data to the medium 701 after processing is completed. A variety of mechanisms are known for managing data movement between the medium 701 and the integrated circuit memory element 604, 702, and the invention is not limited thereto. The invention is not limited to a particular memory system 604 or storage system 606.

Although computer system 600 is shown by way of example as one type of computer system upon which various aspects of the invention may be practiced, it should be appreciated that aspects of the invention are not limited to being implemented on the computer system as shown in FIG. 6. Various aspects of the invention may be practiced on one or more computers having a different architecture or components than that shown in FIG. 6.

Computer system 600 may be a general-purpose computer system that is programmable using a high-level computer programming language. Computer system 600 may be also implemented using specially programmed, special purpose hardware. In computer system 600, processor 603 is typically a commercially available processor such as the Pentium, Core, Core Vpro, Xeon, or Itanium class processors available from the Intel Corporation. Many other processors are available. Such a processor usually executes an operating system which may be, for example, operating systems provided by Microsoft Corporation or Apple Corporation, including versions for PCs as well as mobile devices, iOS, Android OS operating systems, or UNIX available from various sources. Many other operating systems may be used.

Various embodiments of the present invention may be programmed using an object-oriented programming language, such as SmallTalk, Python, Java, C++, Ada, or C# (C-Sharp). Other object-oriented programming languages may also be used. Alternatively, functional, scripting, and/or logical programming languages may be used. Various aspects of the invention may be implemented in a non-programmed environment (e.g., documents created in HTML, XML or other format that, when viewed in a window of a browser program, render aspects of a graphical-user interface (GUI) or perform other functions). Various aspects of the invention may be implemented using various Internet technologies such as, for example, the Common Gateway Interface (CGI) script, PHP Hyper-text Preprocessor (PHP), Active Server Pages (ASP), HyperText Markup Language (HTML), Extensible Markup Language (XML), Java, JavaScript and open source libraries for extending Javascript, Asynchronous JavaScript and XML (AJAX), Flash, and other programming methods. Further, various aspects of the present invention may be implemented in a cloud-based computing platform, such as the EC2 platform available commercially from Amazon.com (Seattle, Wash.), among others. Various aspects of the invention may be implemented as programmed or non-programmed elements, or any combination thereof.

Methods of Use

Described herein are real-time musical translation devices (RETMs) and related software suitable for receiving real-time input (e.g., a text, audio or spoken message) containing information to be conveyed, and converting that input to a patterned musical message (e.g., a song or melody) to treat an indication in a user, such as a disease, disorder, or condition described herein. The user may have a cognitive impairment, a behavioral impairment, or a learning impairment. The cognitive impairment, behavioral impairment, or learning impairment may be chronic (e.g., lasting for more than 1 month, 2 months, 3 months, 6 months, 1 year, 2 years, 5 years, or longer) or acute (e.g., lasting for less than 2 years, 1 year, 6 months, 4 months, 2 months, 1 month, 2 weeks, 1 week, or less). Exemplary diseases, disorders, or conditions, such as cognitive, behavioral, or learning impairments, in a user include autism spectrum disorder, attention deficit disorder, attention deficit hyperactivity disorder, aphasia, dementia, dyslexia, dysphasia, apraxia, stroke, traumatic brain injury, schizophrenia, schizoaffective disorder, depression, bipolar disorder, post-traumatic stress disorder, Alzheimer's disease, Parkinson's disease, Down's syndrome, Prader Willi syndrome, Smith Magenis syndrome, age-related cognitive impairment, indications that include learning disability and/or intellectual disability, anxiety, stress, brain surgery, surgery, and a language comprehension impairment or other neurological disorder.

It will be appreciated that an RETM and related software described herein can be used to enhance communication and interaction between a user and the user's family members, care providers, and the like. For example, the RETM may be used to convey important information to a user who is at least partially self-reliant, including information about medical and other appointments, nutrition, clothing, personal and general news, and the like.

It will also be appreciated that an RETM and related software described herein can be used to provide training in musical therapy, such as for users having dyslexia or aphasia. Standardized training modules may be developed and presented to the user to allow for standardized, uniform therapy, and to allow caretakers and medical personnel to measure the clinical benefit to the user. A user may also use the RETM as a musical therapy device, such as a user having expressive aphasia who needs to re-learn how to speak.

It will be appreciated that an RETM and related software described herein can be used by a user in combination with an additional treatment. The additional treatment may be a pharmaceutical agent (e.g., a drug) or a therapy, such as speech language therapy, physical therapy, occupational therapy, psychological therapy, neurofeedback, diet alteration, cognitive therapy, academic instruction and/or tutoring, exercise, and the like. In an embodiment, the additional treatment employed may achieve a desired effect for the same disease, disorder, or condition, or may achieve a different effect. The additional treatment may be administered simultaneously with use of the RETM, or may be administered before or after use of the RETM. Exemplary pharmaceutical agents administered in combination with use of the RETM include a pain reliever (e.g., aspirin, acetaminophen, ibuprofen), an antidepressant (e.g., citalopram, escitalopram, fluoxetine, fluvoxamine, paroxetine, sertraline, trazodone, nefazodone, vilazodone, vortioxetine, duloxetine, venlafaxine), an antipsychotic (e.g., paliperidone, olanzapine, risperidone, or aripiprazole), a dopamine analog (e.g., levodopa or carbidopa), a cholinesterase inhibitor (e.g., donepezil, galantamine, or rivastigmine), a stimulant (e.g., dextroamphetamine, dexmethylphenidate, methylphenidate), or a vitamin or supplement. In some cases, use of an RETM by a user may result in a modified (e.g., reduced) dosage of a pharmaceutical agent required to achieve a desired therapeutic effect. For example, a user receiving treatment for depression with an anti-depressant may require a lower dosing regimen of said anti-depressant during or after treatment with an RETM.

Autism spectrum disorder (ASD) affects communication and behavior in an individual. A person affected with ASD may have difficulty in communication and interaction with other people, restricted interests, repetitive behaviors, or exhibit other symptoms that may affect his or her ability to function properly and assimilate into society. In an embodiment, a user with ASD may be treated with an RETM described herein. A user having ASD may be further administered a treatment for irritability or another symptom of ASD, such as aripiprazole or risperidone. In an embodiment, the dosage of aripiprazole or risperidone administered to a user with ASD is between 0.1 mg and 50 mg. In an embodiment, a user with ASD is administered aripiprazole or risperidone in conjunction with using an RETM described herein, which may result in a modified (e.g., reduced) dosing regimen to attain a beneficial therapeutic effect.

Attention deficit disorder (ADD) and attention deficit hyperactivity disorder (ADHD) are disorders marked by a pattern of inattention or hyperactivity/impulsivity that interferes with daily life. For example, an individual with ADD or ADHD may exhibit a range of behavioral problems, such as difficulty attending to instruction or focusing on a task. In an embodiment, a user with ADD and/or ADHD may be treated with an RETM described herein. A user having ADD or ADHD may further be administered a treatment, such as methylphenidate (Ritalin) or a mixed amphetamine salt (Adderall or Adderall XR), to reduce or alleviate a symptom of the disorder. The dosage of methylphenidate or a mixed amphetamine salt administered to a user is between 5 mg and 100 mg. In an embodiment, a user with ADD or ADHD is administered methylphenidate or a mixed amphetamine salt in conjunction with using an RETM described herein which may result in a modified (e.g., reduced) dosing regimen to attain a beneficial therapeutic effect.

Depression is a mood disorder resulting in a persistent feeling of sadness and/or loss of interest in daily activities. It often presents with low self-esteem, fatigue, headaches, digestive problems, or low energy, and may negatively impact one's life by affecting personal and professional relationships and general health. In an embodiment, a user with depression may be treated with an RETM described herein. A user with depression may further be administered a treatment to reduce or alleviate a symptom of the disease, such as a selective serotonin reuptake inhibitor (SSRI), e.g., citalopram (Celexa), escitalopram (Lexapro), fluoxetine (Prozac), fluvoxamine (Luvox), paroxetine (Paxil), or sertraline (Zoloft). In an embodiment, the dosage of citalopram, escitalopram, fluoxetine, fluvoxamine, paroxetine, or sertraline administered to a user is between 0.1 mg and 250 mg. In an embodiment, a user with depression is administered citalopram, escitalopram, fluoxetine, fluvoxamine, paroxetine, or sertraline in conjunction with using an RETM described herein which may result in a modified (e.g., reduced) dosing regimen to attain a beneficial therapeutic effect.

Bipolar disorder is a condition causing extreme mood swings ranging from mania to depression in an individual, including periods of both depression and abnormally elevated mood. In an embodiment, a user with bipolar disorder may be treated with an RETM described herein. A user with bipolar disease may further be administered a treatment to reduce or alleviate a symptom of the disease, such as lithium carbonate, divalproex, and lamotrigine. In an embodiment, the dosage of lithium carbonate, divalproex, and lamotrigine administered to a user is between 100 mg and 5 g. In an embodiment, a user with bipolar disorder is administered lithium carbonate, divalproex, and lamotrigine in conjunction with using an RETM described herein which may result in a modified (e.g., reduced) dosing regimen to attain a beneficial therapeutic effect.

Alzheimer's disease is a progressive neurological degenerative disease believed to be caused by the formation of beta-amyloid plaques in the brain that result in an impairment of memory, cognition, and other thinking skills. In an embodiment, a user with Alzheimer's disease may be treated with an RETM described herein. A user with Alzheimer's disease may further be administered a treatment to reduce or alleviate a symptom of the disease, such as a cholinesterase inhibitor (e.g., donepezil, galantamine, or rivastigmine). In an embodiment, the dosage of donepezil, galantamine, or rivastigmine administered to a user is between 0.1 mg and 100 mg. In an embodiment, a user with Alzheimer's disease is administered donepezil, galantamine, or rivastigmine in conjunction with using an RETM described herein which may result in a modified (e.g., reduced) dosing regimen to attain a beneficial therapeutic effect.

Parkinson's disease is a progressive neurodegenerative disorder that primarily affects the dopamine-producing neurons in the brain, resulting in tremors, stiffness, imbalance, and impairment in movement. In an embodiment, a user with Parkinson's disease may be treated with an RETM described herein. A user with Parkinson's disease may further be administered a treatment to reduce or alleviate a symptom of the disease, such as levodopa or carbidopa. In an embodiment, the dosage of levodopa or carbidopa administered to a user is between 1 mg and 100 mg. In an embodiment, a user with Parkinson's disease is administered levodopa or carbidopa in conjunction with using an RETM described herein which may result in a modified (e.g., reduced) dosing regimen to attain a beneficial therapeutic effect.

Schizophrenia is a disorder that affects the perception of the affected, often resulting in hallucinations, delusions, and severely disoriented thinking and behavior. In an embodiment, a user with schizophrenia may be treated with an RETM described herein. A user with schizophrenia may further be administered a treatment to reduce or alleviate a symptom of the disorder, such as haloperidol, olanzapine, risperidone, quetiapine, or aripiprazole. In an embodiment, the dosage of haloperidol, olanzapine, risperidone, quetiapine, or aripiprazole administered to a user is between 1 mg and 800 mg. For example, in an embodiment, a user with schizophrenia is administered haloperidol, olanzapine, risperidone, quetiapine, or aripiprazole in conjunction with using an RETM described herein which may result in a modified (e.g., reduced) dosing regimen to attain a beneficial therapeutic effect.

Schizoaffective disorder is a condition in which an individual experiences symptoms of schizophrenia coupled with a mood disorder, such as bipolar disorder or depression. In an embodiment, a user with schizoaffective disorder may be treated with an RETM described herein. A user with schizoaffective disorder may further be administered a treatment to reduce or alleviate a symptom of the disease, such as paliperidone or another first- or second-generation antipsychotic, possibly with the addition of an anti-depressant. In an embodiment, the dosage of anti-psychotic and/or anti-depressant administered to a user is between 0.5 mg and 50 mg. In an embodiment, a user with schizoaffective disorder is administered paliperidone or another first- or second-generation antipsychotic in conjunction with using an RETM described herein which may result in a modified (e.g., reduced) dosing regimen to attain a beneficial therapeutic effect.

The device may be used in conjunction with an additional agent to achieve a synergistic effect. For example, in the case of a user having schizophrenia, use of the device with an anti-psychotic agent may allow for lowering of the dose of anti-psychotic agent in the user (e.g., relative to the dose of the anti-psychotic prescribed prior to use of the device). In another example, use of the device with an anti-psychotic agent may reduce persistent symptoms of schizophrenia that have continued despite optimizing the anti-psychotic medication regimen.

A user with a disease, disorder, or condition described herein may be diagnosed or identified as having the disease, disorder, or condition. In an embodiment, the user has been diagnosed by a physician. In an embodiment, the user has not been diagnosed or identified as having a disease, disorder, or condition. In these cases, the user may have one or more symptoms of a cognitive impairment, a behavioral impairment, or a learning impairment (e.g., as described herein) but has not received a diagnosis, e.g., by a physician.

In an embodiment, a user may be either a male or female. In an embodiment, the user is an adult (e.g., over 18 years of age, over 35 years of age, over 50 years of age, over 60 years of age, over 70 years of age, or over 80 years of age). In an embodiment, the user is a child (e.g., less than 18 years of age, less than 10 years of age, less than 8 years of age, less than 6 years of age, or less than 4 years of age).

While the embodiments discussed above relate to translating words or text to song in order to facilitate word or syntax comprehension or memory, other methods of use should be understood to be within the scope of this disclosure. For example, in many current video games, including RPGs (role-playing games), action games, simulation games, and strategy games, users are presented with dialog with other characters in the game, with a narrator, or as a set of instructions on how to play the game. In one embodiment, the RETM may be used by game developers to convert whatever text is presented in the game to song during the course of gameplay, and for instructions and aspects of setting up and running the game. Such an embodiment may provide enhanced enjoyment of the game for both users with and without disorders. In addition, it may increase accessibility of these videogames to users with language- or text-related impairments as described above.

In another example, it will be appreciated that virtual digital assistants (e.g., Alexa by Amazon) are often interacted with, in homes and businesses, through devices such as smart speakers. Such virtual assistants may be modified according to aspects described herein to respond through song to the respondent, rather than through spoken voice, to allow optimal comprehension of the system's response, thereby returning information on products music, news, weather, sports, home system functioning and more to a person in need of song for optimal comprehension and functioning.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:
1. A method of transforming textual input to a musical score comprising:
receiving a first text input;
transliterating the first text input into a standardized phonemic representation of the first text input;
determining for the phonemic text input, a plurality of spoken pause lengths and a plurality of spoken phoneme lengths;
mapping the plurality of spoken pause lengths to a respective plurality of sung pause lengths;
mapping the plurality of spoken phoneme lengths to a respective plurality of sung phoneme lengths;
generating, from the plurality of sung pause lengths and the plurality of sung phoneme lengths, a first timed text input;
generating, based on at least one user preference of a user, a first plurality of matching metrics for each of a respective plurality of portions of the first timed text input against a plurality of melody segments;
generating a first patterned musical message from the first timed text input and the plurality of melody segments based at least in part on the first plurality of matching metrics;
receiving feedback information indicating a response of the user to the first patterned musical message;
executing a machine-learning optimization algorithm to update the at least one user preference of the user using a training data set including the feedback information;
receiving a second text input;
generating a second timed text input based on the second text input;
generating a second plurality of matching metrics based on the second timed text input, the second plurality of matching metrics being determined based on the at least one updated user preference of the user; and
generating a second patterned musical message from the second timed text input based at least in part on the second plurality of matching metrics.
2. The method of claim 1, wherein the method is performed in real-time or in near-real-time, and further comprises causing the first patterned musical message to be played audibly on a transducer, and wherein the feedback information indicates a response of the user to the first patterned musical message being played audibly on the transducer.

3. The method of claim 2, further comprising causing the second patterned musical message to be played audibly on the transducer.

4. The method of claim 1, wherein the first patterned musical message is expected to optimize, for a user, at least one of an understanding of the first text input and a recall of the first text input.

5. The method of claim 1, further comprising providing to a user a visual image relating to the first patterned musical message aimed at enhancing comprehension and learning.

6. The method of claim 1, wherein the first patterned musical message is presented to a user having a cognitive impairment, a behavioral impairment, or a learning impairment.

7. The method of claim 6, wherein the user has a comprehension disorder, including at least one of autism spectrum disorder, attention deficit disorder, attention deficit hyperactivity disorder, aphasia, dementia, dyspraxia, dyslexia, dysphasia, apraxia, stroke, traumatic brain injury, brain surgery, surgery, schizophrenia, schizoaffective disorder, depression, bipolar disorder, post-traumatic stress disorder, Alzheimer's disease, Parkinson's disease, age-related cognitive impairment, a language comprehension impairment, an intellectual disorder, a developmental disorder, stress, anxiety, Williams syndrome, Prader Willi syndrome, Smith Magenis syndrome, Bardet Biedl syndrome, or Down's syndrome or other neurological disorder.

8. The method of claim 1, wherein the first text input is received as a spoken message or a written message.

9. The method of claim 1, wherein the user selects the first text input from a plurality of texts.

10. The method of claim 1, further comprising:
generating a textual message relating to the first text input and representing an output message to be displayed to a user;
modifying at least one character of the textual message in a manner expected to optimize at least one of the user's understanding and recall of the textual message as seen on a visual display; and
displaying the modified textual message on a display device.

11. The method of claim 10, wherein modifying the at least one character of the textual message in the manner expected to optimize the user's understanding and/or recollection of the textual message includes at least one of removing or modifying at least one segment of the at least one character, modifying a size of the at least one character relative to other characters in the textual message, and modifying a display time of the at least one character relative to the other characters in the textual message.

12. The method of claim 1, wherein generating the first patterned musical message from the first timed text input and the plurality of melody segments based at least in part on the first plurality of matching metrics comprises:
accessing pitch information and timing information about a note in a melody segment; and
setting a pitch and a timing for a phoneme in the first timed text input based on the pitch information and the timing information.

13. The method of claim 1, wherein the output device is at least one of a virtual reality device, an augmented reality headset device, and a smart speaker executing a digital personal assistant.

14. The method of claim 1, wherein the second text input is received as a spoken message or a written message.

15. The method of claim 1, wherein the user selects the second text input from a plurality of texts.

16. A real time musical translation device (RETM) comprising:
an input interface;
a processor;
an audio output component; and
a memory communicatively coupled to the processor and comprising instructions that when executed by the processor cause the processor to:
receive a first text input from the input interface;
determine, for the first text input, a plurality of spoken pause lengths and a plurality of spoken phoneme lengths;
map the plurality of spoken pause lengths to a respective plurality of sung pause lengths;
map the plurality of spoken phoneme lengths to a respective plurality of sung phoneme lengths;
generate, from the plurality of sung pause lengths and the plurality of sung phoneme lengths, a first timed text input;
generate, based on at least one user preference of a user, a first plurality of matching metrics for each of a respective plurality of portions of the first timed text input against a plurality of melody segments;
generate a first patterned musical message from the first timed text input and the plurality of melody segments based at least in part on the first plurality of matching metrics;
output the first patterned musical message using the audio output component;
receive feedback information indicating a response of the user to the first patterned musical message being output using the audio output component;
execute a machine-learning optimization algorithm to update the at least one user preference of the user using a training data set including the feedback information;
receive a second text input;
generate a second timed text input based on the second text input;
generate a second plurality of matching metrics based on the second timed text input, the second plurality of matching metrics being determined based on the at least one updated user preference of the user; and
generate a second patterned musical message from the second timed text input based at least in part on the second plurality of matching metrics.

17. The RETM of claim 16, further comprising a display device, wherein the processor is further configured to provide to a user a visual image on the display device, the visual image relating to the first patterned musical message.

18. The RETM of claim 17, wherein the display device is incorporated into the output device.

19. The RETM of claim 16, wherein the processor is further configured to:
generate a textual message relating to the first text input and representing an output message to be displayed to a user;
modify at least one character of the textual message in a manner expected to optimize the user's understanding of the textual message; and
display the modified textual message on the display device.

20. The RETM of claim 19, wherein the processor is configured to modify the at least one character of the textual message in the manner expected to optimize the user's understanding and/or recollection of the textual message by at least one of removing or modifying at least one segment of the at least one character, modifying a size of the at least one character relative to other characters in the textual message, and modifying a display time of the at least one character relative to the other characters in the textual message.

21. The RETM of claim 16, wherein the first patterned musical message is presented to a user having a cognitive impairment, a behavioral impairment, or a learning impairment.

22. The RETM of claim 21, wherein the user has a comprehension disorder, including at least one of autism spectrum disorder, attention deficit disorder, attention deficit hyperactivity disorder, aphasia, dementia, dyspraxia, dyslexia, dysphasia, apraxia, stroke, traumatic brain injury, brain surgery, surgery, schizophrenia, schizoaffective disorder, depression, bipolar disorder, post-traumatic stress disorder, Alzheimer's disease, Parkinson's disease, age-related cognitive impairment, a language comprehension impairment, an intellectual disorder, a developmental disorder, stress, anxiety, Williams syndrome, Prader Willi syndrome, Smith Magenis syndrome, Bardet Biedl syndrome, or Down's syndrome or other neurological disorder.

23. A method of transforming textual input to a musical score for improving a cognitive process in a user comprising:
providing the user with access to a real-time musical translation device (RETM), wherein the RETM comprises:
an input interface;
a processor;
an audio output component; and
a memory communicatively coupled to the processor and comprising instructions that when executed by the processor cause the processor to:
receive a first text input from the input interface;
determine, for the first text input, a plurality of spoken pause lengths and a plurality of spoken phoneme lengths;
map the plurality of spoken pause lengths to a respective plurality of sung pause lengths;
map the plurality of spoken phoneme lengths to a respective plurality of sung phoneme lengths;
generate, from the plurality of sung pause lengths and the plurality of sung phoneme lengths, a first timed text input;
generate, based on at least one user preference of a user, a first plurality of matching metrics for each of a respective plurality of portions of the first timed text input against a plurality of melody segments;
generate a first patterned musical message from the first timed text input and the plurality of melody segments based at least in part on the first plurality of matching metrics;
output the first patterned musical message to the user using the audio output component;
receive feedback information indicating a response of the user to the first patterned musical message being output using the audio output component;
execute a machine-learning optimization algorithm to update the at least one user preference of the user using a training data set including the feedback information;
receive a second text input;
generate a second timed text input based on the second text input;
generate a second plurality of matching metrics based on the second timed text input, the second plurality of matching metrics being determined based on the at least one updated user preference of the user; and
generate a second patterned musical message from the second timed text input based at least in part on the second plurality of matching metrics.

24. The method of claim 23, wherein the first patterned musical message is expected to optimize a user's understanding of the first text input.

25. The method of claim 23, further comprising providing to the user a visual image relating to the first patterned musical message.

26. The method of claim 23, wherein the first patterned musical message is presented to a user having a cognitive impairment, a behavioral impairment, or a learning impairment.

27. The method of claim 26, wherein the user has a comprehension disorder, including at least one of autism spectrum disorder, attention deficit disorder, attention deficit hyperactivity disorder, aphasia, dementia, dyspraxia, dyslexia, dysphasia, apraxia, stroke, traumatic brain injury, brain surgery, surgery, schizophrenia, schizoaffective disorder, depression, bipolar disorder, post-traumatic stress disorder, Alzheimer's disease, Parkinson's disease, age-related cognitive impairment, a language comprehension impairment, an intellectual disorder, a developmental disorder, stress, anxiety, Williams syndrome, Prader Willi syndrome, Smith Magenis syndrome, Bardet Biedl syndrome, or Down's syndrome or other neurological disorder.

28. The method of claim 23, wherein the first patterned message is presented to a user for at least one of enhancing comprehension, improving communication, and increasing social interaction.

29. The method of claim 23, further comprising:
tracking a performance of the user over successive uses of the RETM; and
determining, from the performance of the user, a measure of improvement of the user in at least one area.

30. The method of claim 23, wherein the first text input is received as a spoken message or a written message.

31. The method of claim 23, further comprising:
generating a textual message relating to the first text input and representing an output message to be displayed to a user;
modifying at least one character of the textual message in a manner expected to optimize at least one of the user's understanding and recall of the textual message as seen on a visual display; and
displaying the modified textual message on a display device.

32. The method of claim 31, wherein modifying the at least one character of the textual message in the manner expected to optimize the user's understanding and/or recollection of the textual message includes at least one of removing or modifying at least one segment of the at least one character, modifying a size of the at least one character relative to other characters in the textual message, and modifying a display time of the at least one character relative to the other characters in the textual message.

33. The method of claim 23, wherein generating the first patterned musical message from the first timed text input and the plurality of melody segments based at least in part on the first plurality of matching metrics comprises:
accessing pitch information and timing information about a note in a melody segment; and setting a pitch and a timing for a phoneme in the first timed text input based on the pitch information and the timing information.

\* \* \* \* \*